United States Patent
Lynn et al.

(10) Patent No.: US 11,097,037 B2
(45) Date of Patent: Aug. 24, 2021

(54) SYSTEMS AND METHODS FOR LEUKOREDUCING A RED BLOOD CELL-CONTAINING FLUID AND CONCENTRATED RED BLOOD CELLS

(71) Applicant: Fenwal, Inc., Lake Zurich, IL (US)

(72) Inventors: Daniel R. Lynn, Spring Grove, IL (US); Daryl R. Calhoun, Gurnee, IL (US)

(73) Assignee: Fenwal, Inc., Lake Zurich, IL (US)

( * ) Notice: Subject to any disclaimer, the term of this patent is extended or adjusted under 35 U.S.C. 154(b) by 174 days.

(21) Appl. No.: 16/439,887

(22) Filed: Jun. 13, 2019

(65) Prior Publication Data

US 2019/0290814 A1  Sep. 26, 2019

Related U.S. Application Data

(62) Division of application No. 14/677,319, filed on Apr. 2, 2015, now Pat. No. 10,376,620.

(51) Int. Cl.
*A61M 1/02* (2006.01)
*A61M 1/36* (2006.01)
(Continued)

(52) U.S. Cl.
CPC ........ *A61M 1/0218* (2014.02); *A61M 1/0272* (2013.01); *A61M 1/265* (2014.02);
(Continued)

(58) Field of Classification Search
CPC .. A61M 1/0218; A61M 1/0272; A61M 1/265; A61M 1/34; A61M 1/3633; A61M 2202/0429; C12N 5/0641
See application file for complete search history.

(56) References Cited

U.S. PATENT DOCUMENTS 4,453,927 A   6/1984  Sinko
4,753,729 A   6/1988  Schoendorfer et al.
(Continued)

FOREIGN PATENT DOCUMENTS

EP   1582228 A1   10/2005
EP   2818189 A1   12/2014
(Continued)

OTHER PUBLICATIONS

Snyder, E.L; et al., "Role of Microaggregate Blood Filtration in Clinical Medicine," Department of Laboratory Medicine, Yale University, School of Medicine, Transfusion, vol. 23, No. 6, pp. 460-470 (1983).
(Continued)

*Primary Examiner* — John Kim
(74) *Attorney, Agent, or Firm* — Cook Alex Ltd.

(57) ABSTRACT

Systems and methods are provided for separating a red blood cell-containing fluid into separated red blood cells and another fluid constituent. A suitable system includes a disposable fluid flow circuit and a durable, reusable separation system, with the circuit being mounted onto or otherwise associated with the separation system. The circuit includes a membrane separator for separating the fluid into its constituent parts, as well as a leukoreduction filter. The leukoreduction filter may be used before or after the red blood cell-containing fluid has been passed into the membrane separator. The red blood cell-containing fluid (if the leukoreduction filter is positioned upstream of the membrane separator) or the separated red blood cells (if the leukoreduction filter is positioned downstream of the membrane separator) may also be passed through a microaggregate filter prior to passing through the leukoreduction filter.

18 Claims, 5 Drawing Sheets

(51) Int. Cl.
*A61M 1/34* (2006.01)
*A61M 1/26* (2006.01)
*C12N 5/078* (2010.01)

(52) U.S. Cl.
CPC ............ *A61M 1/34* (2013.01); *A61M 1/3633* (2013.01); *C12N 5/0641* (2013.01); *A61M 2202/0429* (2013.01)

(56) References Cited

U.S. PATENT DOCUMENTS

| | | |
|---|---|---|
| 4,776,964 A | 10/1988 | Schoendorfer et al. |
| 4,898,573 A | 2/1990 | Takenaka et al. |
| 4,954,251 A | 9/1990 | Barnes et al. |
| 5,135,667 A | 8/1992 | Schoendorfer |
| 5,194,145 A | 3/1993 | Schoendorfer |
| 5,344,561 A | 9/1994 | Pall et al. |
| 6,468,291 B2 | 10/2002 | Bates et al. |
| 7,008,393 B2 | 3/2006 | Robinson et al. |
| 2006/0180542 A1 | 8/2006 | Mari et al. |
| 2015/0265755 A1 | 9/2015 | Lynn et al. |
| 2015/0265758 A1 | 9/2015 | Verri et al. |
| 2015/0265954 A1 | 9/2015 | Lynn et al. |

FOREIGN PATENT DOCUMENTS

| | | |
|---|---|---|
| EP | 3023112 A1 | 5/2016 |
| JP | 2011083312 A | 4/2011 |
| WO | 00/62891 | 10/2000 |
| WO | 2012125457 A1 | 9/2012 |
| WO | WO 2014/016198 A1 | 1/2014 |
| WO | 2014039086 A1 | 3/2014 |

OTHER PUBLICATIONS

Wortham, Samuel T.; et al., "A Brief History of Blood Filtration: Clot Screens, Microaggregate Removal, and Leukocyte Reduction," Transfusion Medicine Reviews, vol. 17, No. 3, Jul. 2003.
International Search Report and Written Opinion for PCT Patent Application No. PCT/US2016/019677, dated Aug. 19, 2016, 6 pages.

SYSTEMS AND METHODS FOR LEUKOREDUCING A RED BLOOD CELL-CONTAINING FLUID AND CONCENTRATED RED BLOOD CELLS

RELATED APPLICATIONS

This application is a divisional of U.S. patent application Ser. No. 14/677,319, filed Apr. 2, 2015 and issued as U.S. Pat. No. 10,376,620, which is hereby incorporated herein by reference.

BACKGROUND

Field of the Disclosure

The invention relates to blood separation systems and methods. More particularly, the invention relates to blood separation systems and methods also involving leukoreduction of the blood or of a separated cellular blood component.

Description of Related Art

Traditional blood collection continues to rely heavily on manual collection of whole blood from healthy donors through blood drives, from donor visits to blood centers or hospitals and the like. In typical manual collection, whole blood is collected by simply flowing it, under the force of gravity and venous pressure, from the vein of the donor into a collection container. The amount of whole blood drawn is typically a "unit," which is about 450 ml.

More specifically, such a collection typically employs a pre-assembled arrangement of tubing and containers or bags, including a flexible plastic primary container or bag for receiving a unit of whole blood from a donor and one or more "satellite" containers or bags. The blood is first collected in the primary container, which also contains an anticoagulant (typically, but not exclusively, containing sodium citrate, phosphate, and dextrose—often referred to as CPD). A preservative (often called an "additive solution" or AS, and commonly containing a saline, adenine, and glucose medium—which is referred to as SAG) may be included as part of a larger assembly of bags and tubes that are used in processing after the blood is collected.

After collection of a unit of whole blood, it is common practice in blood banking to transport the unit of whole blood, with connected tubing and containers, to a blood component processing laboratory, commonly referred to as a "back lab," for further processing. Further processing usually entails manually loading the primary container and associated tubing and satellite containers into a centrifuge to separate the whole blood into components such as concentrated red cells and platelet-rich or platelet-poor plasma. These components are then manually expressed from the primary container into other pre-connected satellite containers, and may be again centrifuged to separate the platelets from plasma. Subsequently, the blood components may be leukoreduced (i.e., have the white blood cells or leukocytes contained therein removed) by filtration for further processing or storage. In short, this process is time consuming, labor intensive, and subject to possible human error.

While many of the prior blood separation apparatus and procedures have employed centrifugal separation principles, there is another class of devices that employs relatively rotating surfaces, at least one of which carries a porous membrane. Typically the device employs an outer stationary housing and an internal spinning rotor covered by a porous membrane. Detailed descriptions of membrane separators may be found in U.S. Pat. Nos. 5,194,145; 4,776,964; 4,753,729; and 5,135,667, all of which are incorporated by reference herein.

Such systems may include a membrane-covered spinner having an interior collection system disposed within a stationary shell or housing. Alternatively, an inner surface of the stationary housing may be covered by a membrane, or both the spinner and the housing may include associated membranes. For purposes of this description, these will be referred to as membrane separators. In such membrane separators, blood is fed into an annular space or gap between the spinner and the shell and moves along the longitudinal axis of the shell toward an exit region. Plasma passes through the membrane and exits through an outlet port, while the remaining cellular blood components (red blood cells, platelets, and white cells) remain in the gap and move to the exit region between the spinner and the shell. Membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane.

While membrane separators have been widely used for the collection of plasma, they have not typically been used for the collection of other blood components, specifically red blood cells. One example of a membrane separator used in the collection of separated red blood cells is described in PCT Patent Application Publication No. WO 2014/039086 A1, which is incorporated by reference in its entirety.

The subject matter disclosed herein provides further advances in membrane separators, particularly in terms of the reduction of leukocytes in a final collected cellular blood component.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended.

In one aspect, a fluid flow circuit is provided for separating an anticoagulated red blood cell-containing fluid into separated red blood cells and another fluid constituent. The fluid flow circuit includes a membrane separator including an inlet port and a red blood cell outlet port and configured to separate an anticoagulated red blood cell-containing fluid into separated red blood cells and another fluid constituent. An inlet flow path is in fluid communication with the inlet port and a fluid source container for flowing anticoagulated red blood cell-containing fluid from the fluid source container to the inlet port, with a leukoreduction filter being associated with the inlet flow path.

In another aspect, a method is provided for separating an anticoagulated red blood cell-containing fluid into separated red blood cells and another fluid constituent. The method involves providing an anticoagulated red blood cell-containing fluid and flowing it through an inlet flow path, into a membrane separator. The anticoagulated red blood cell-containing fluid is separated into separated red blood cells and another fluid constituent, and the separated red blood cells are flowed out of the membrane separator via an outlet flow path. Prior to the anticoagulated red blood cell-containing fluid entering the membrane separator, it is leukoreduced, such as by passing it through a leukocyte reduction filter associated with the inlet flow path.

In yet another aspect, a fluid flow circuit is provided for separating a red blood cell-containing fluid into separated red blood cells and another fluid constituent. The fluid flow circuit includes a membrane separator having an inlet port and a red blood cell outlet port. An inlet flow path is in fluid communication with the inlet port and an outlet flow path is associated with the red blood cell outlet port, with a leukoreduction filter being associated with the outlet flow path. A microaggregate filter is positioned between the red blood cell outlet port and the leukoreduction filter.

In another aspect, a method is provided for separating a red blood cell-containing fluid into separated red blood cells and another fluid constituent. The method involves providing a red blood cell-containing fluid and flowing it through an inlet flow path, into a membrane separator. The red blood cell-containing fluid is separated into separated red blood cells and another fluid constituent, and the separated red blood cells are flowed out of the membrane separator via an outlet flow path, with the separated red blood cells passing through a microaggregate filter and a leukoreduction filter.

DESCRIPTION OF THE ILLUSTRATED EMBODIMENTS

The embodiments disclosed herein are for the purpose of providing an exemplary description of the present subject matter. They are, however, only exemplary and not exclusive, and the present subject matter may be embodied in various forms. Therefore, specific details disclosed herein are not to be interpreted as limiting the subject matter as defined in the accompanying claims.

Figure 1:
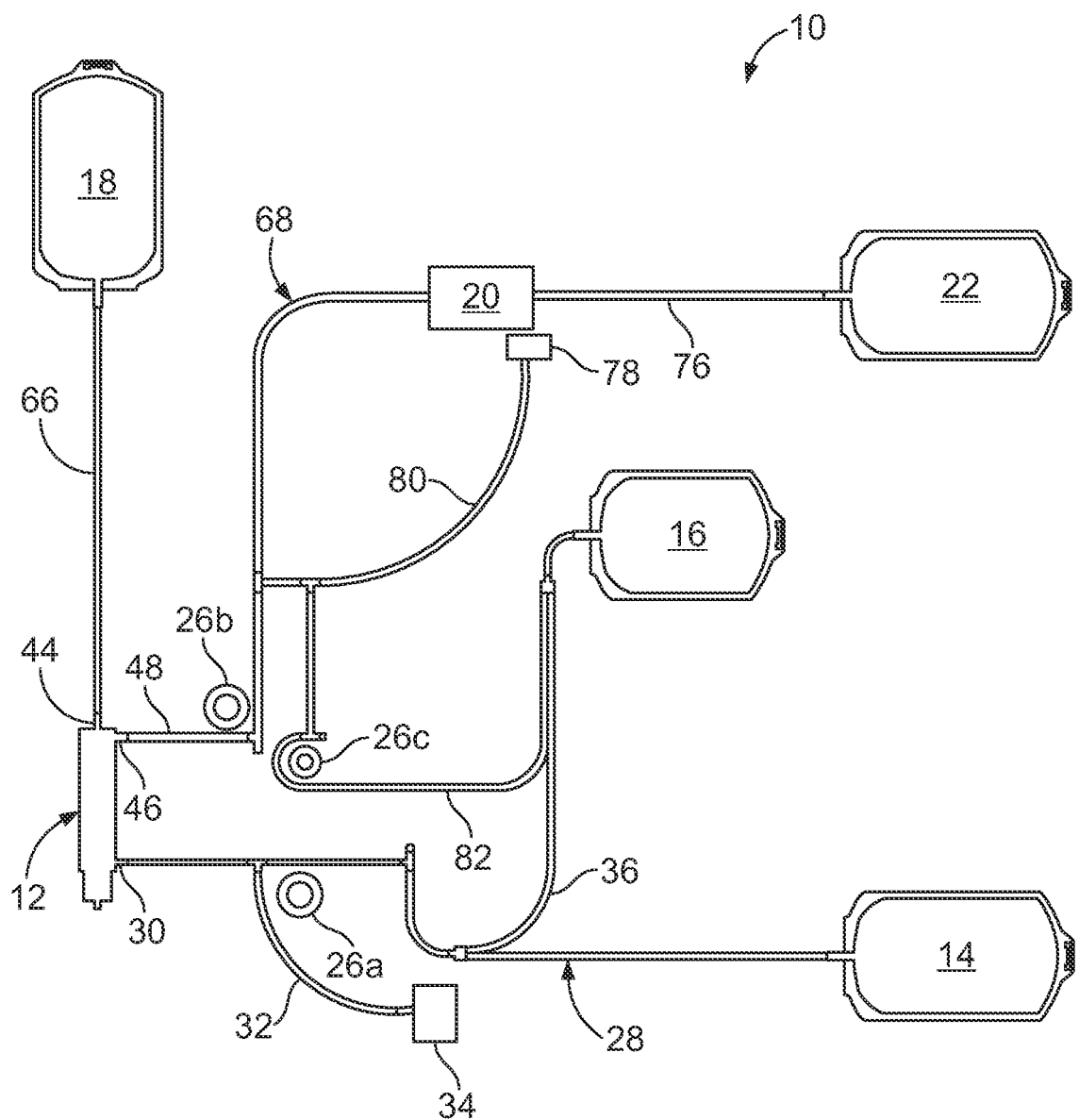
FIG. 1 is a front elevational view of an exemplary disposable fluid flow circuit according to an aspect of the present disclosure.
Figure 2:
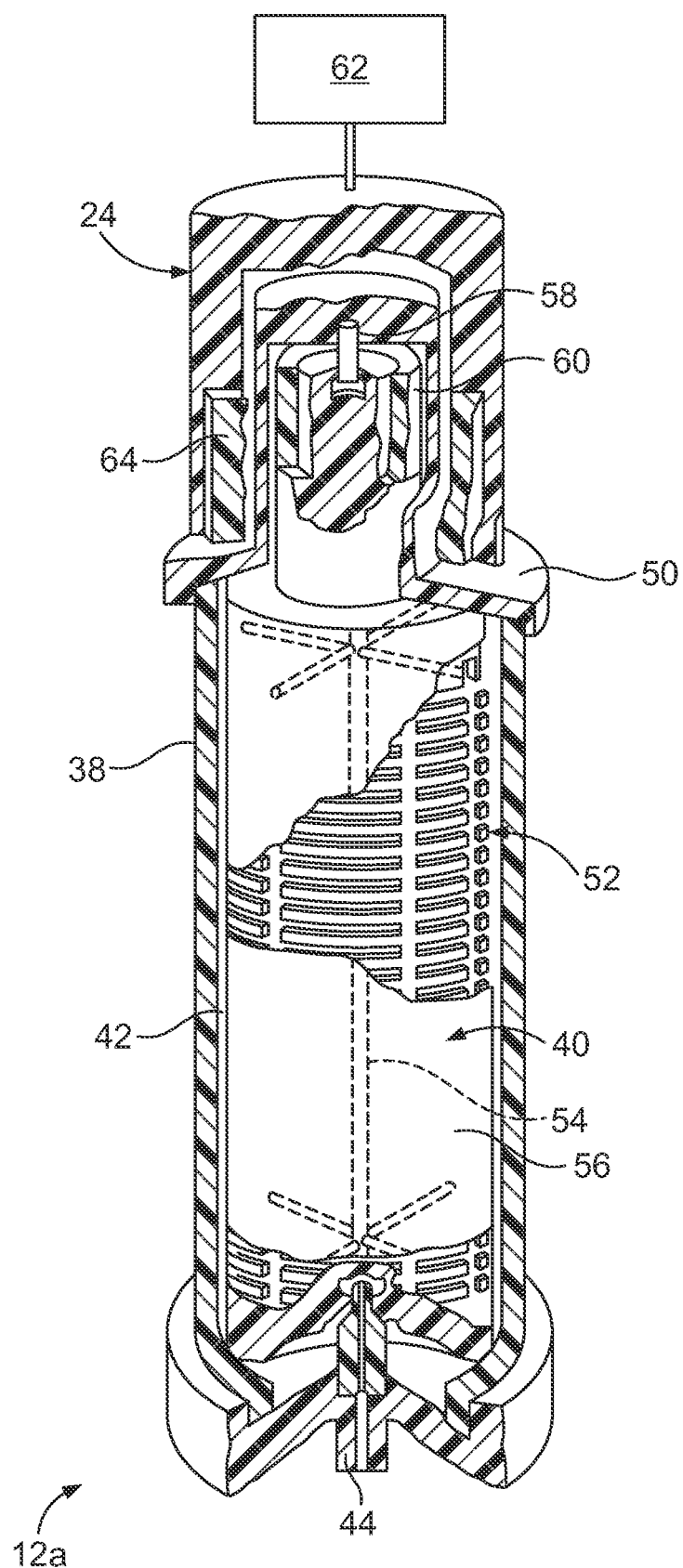
FIG. 2 is a perspective view of a membrane separator of the fluid flow circuit of FIG. 1, in partial cross section and with portions removed to show detail.

FIG. 1 illustrates a disposable fluid flow circuit 10 having a membrane separator 12 (illustrated in greater detail as a spinning membrane separator 12a in FIG. 2) for use in combination with a durable, reusable separation system (which controls flow through the fluid flow circuit 10) to separate red blood cells from a red blood cell-containing fluid (e.g., anticoagulated whole blood). The disposable fluid flow circuit 10 and durable separation system may be similarly configured to the disposable fluid circuit and durable blood separation system described in PCT Patent Application Publication No. WO 2014/039086 A1. While the following description may refer primarily to the separation of red blood cells from whole blood, it should be understood that the present disclosure is not limited to separation of red blood cells from whole blood, but may encompass separation of red blood cells from any red blood cell-containing fluid.

The disposable fluid flow circuit 10 as illustrated in FIG. 1 includes various components interconnected by flow paths, which may be variously configured. In one embodiment, one or more of the flow paths between the components of the circuit 10 are defined by flexible plastic tubing, but the flow paths may be otherwise configured without departing from the scope of the present disclosure. The fluid flow circuit 10 is preferably fully pre-assembled and pre-sterilized, although certain components thereof (e.g., a fluid source container 14 and additive container 16) may be separately provided and sterilely connected to the circuit 10. More specifically, the illustrated disposable circuit 10 includes a fluid source container 14, an additive container 16, a membrane separator 12, a secondary fluid constituent collection container 18, a leukocyte reduction filter 20, and a red blood cell collection container 22. The circuit 10 may be associated with a separation system by connecting the membrane separator 12 to a separation actuator 24 of the separation system (FIG. 2), while hanging the various containers from hangers or hooks of the separation system. It is also within the scope of the present disclosure for one or more of the containers to be associated with the separation system in a different way (e.g., by placing a container on a horizontal surface, such as a weigh scale). Also, pumps may be provided to control flow through the circuit 10. For example, certain portions of the flow path may be engaged by fluid pumps 26a-26c (e.g., peristaltic pumps) of the separation system, which cause the passage of fluid through the circuit 10. It should be understood that the illustrated circuit 10 is merely exemplary and that differently configured disposable fluid circuits having a membrane separator for separating red blood cells from a red blood cell-containing fluid may be employed without departing from the scope of the present disclosure.

The fluid source container 14 may be any suitable container but is typically a flexible plastic pouch or bag in which a red blood cell-containing fluid (e.g., approximately 450 ml of whole blood) has been previously collected. The container 14 may be separate from the fluid circuit 10 during collection from a fluid source, allowing the red blood cell-containing fluid to be more easily collected and stored before being joined to the rest of the fluid circuit 10, or may be connected with the circuit 10 at the time of collection. Preferably, the container 14 is provided with an amount of anticoagulant prior to (or following) the introduction of the red blood cell-containing fluid into the container 14 and before the anticoagulated fluid is flowed out of the container 14 to prevent premature coagulation.

A flow path 28 (referred to herein as the "inlet flow path") is attached to the fluid source container 14, such as by a sterile connection device or other suitable attachment mechanism, and defines a fluid flow path from the container 14 to an inlet port 30 of the membrane separator 12. The inlet flow path 28 may include additional components (e.g., fluid control valves or clamps) and junctions and branches, such as a flow path branch 32 that may be associated with a pressure sensor 34 of the separation system and/or a flow path branch 36 that may be associated with the additive container 16.

Additionally, it may be preferred for a portion of the inlet flow path 28 to be configured to be acted upon by an inlet pump 26a of the separation system for actively pumping fluid through the inlet flow path 28 and into the membrane separator 12. The configuration of the inlet pump 26a may vary without departing from the scope of the present disclosure, but in one embodiment it is provided as a peristaltic pump that operates by progressive compression or squeezing of a portion of the inlet flow path 28.

FIG. 2 shows a particular embodiment of the membrane separator 12 in greater detail, along with a separation actuator 24 of the separation system. The separator 12a of FIG. 2 employs a membrane on a spinning rotor, and is referred to herein as a spinning membrane separator. The spinning membrane separator 12a includes a generally cylindrical housing 38, mounted concentrically about a longitudinal vertical central axis. An internal member or rotor 40 is mounted within the housing 38, preferably concentrically with the central axis. The rotor 40 is rotatable about the central axis, while the housing 38 remains stationary. The boundaries of the fluid flow path through the spinning membrane separator 12a are generally defined by the gap 42 between the interior surface of the housing 38 and the exterior surface of the rotor 40. The spacing between the housing 38 and the rotor 40 is sometimes referred to as the shear gap 42. A typical shear gap may be approximately 0.025-0.050 inches wide and may be of a uniform dimension along the axis, for example, where the axis of the rotor 40 and housing 38 are coincident. The dimensions of the shear gap 42 may also vary circumferentially, for example, where the rotor 40 and the axis of the housing 38 are offset.

The anticoagulated red blood cell-containing fluid is fed from the inlet flow path 28 into the housing 38 via an inlet port 30 (FIG. 1), which directs the fluid into a fluid flow entrance region in a path tangential to and in fluid communication with the shear gap 42. At an axial end of the cylindrical housing 38 (preferably the end spaced farthest from the inlet port 30), the housing 38 includes an axial outlet port 44 for withdrawal of a secondary fluid constituent (i.e., the fluid component separated from the red blood cells) from the spinning membrane separator 12a. In the orientation of FIG. 2, the spinning membrane separator 12a is oriented to position the axial outlet port 44 at the bottom end of the spinning membrane separator 12a, while FIG. 1 shows the membrane separator 12 oriented to position the axial outlet port 44 at the upper end. It should be understood that different membrane separators may be oriented differently such that, depending on the design of the membrane separator and associated separation system, the membrane separator may be connected to the separation system so as to orient the axial outlet port 44 in any direction without departing from the scope of the present disclosure.

Adjacent to the axial end of the housing 38 having the axial outlet port 44, the housing 38 also has a side or tangential or red blood cell outlet port 46 (FIG. 1) that communicates with the gap 42 between the housing 38 and rotor 40 (FIG. 2) and with a concentrated red cell flow path flow path 48 (FIG. 1) for withdrawing concentrated red blood cells from the separator gap 42. The axial end of the cylindrical housing 38 opposite the axial outlet port 44 may include an end cap 50. The end cap 50 is configured to be at least partially received within the separation actuator 24 of the separation system (FIG. 2) to allow the separation actuator 24 to rotate the rotor 40, as will be described in greater detail.

The rotor 40 is rotatably mounted between the axial ends of the housing 38 and may be provided as a generally cylindrical central mandrel 52, the outer surface of which is shaped to define a series of spaced-apart circumferential grooves or ribs separated by annular lands. The surface channels defined by the circumferential grooves are interconnected by longitudinal grooves. At each end of the mandrel 52, these grooves are in communication with a central orifice or manifold 54.

In the illustrated embodiment, the surface of the rotor 40 is at least partially (and more preferably substantially or entirely) covered by a cylindrical porous membrane 56. The nominal pore size of the membrane 56 may vary, but it may be preferred for the membrane 56 to be configured (including having suitable nominal pore size) to allow plasma (or some other fluid constituent to be separated from red blood cells) to pass through the membrane 56 without allowing the passage of red blood cells therethrough. While the illustrated embodiment places the membrane 56 on the rotor 40, it should be recognized that a membrane could potentially be mounted on the inside surface of the housing 38, facing the gap 42 between the inside surface of the housing wall and the outer surface of the rotor 40, or a membrane could be carried on both the outer surface of the rotor 40 and the inner surface of the housing 38 so that plasma flows through both membranes simultaneously, therefore potentially increasing the separation speed or performance of the spinning membrane separator 12a.

The rotor 40 is mounted in the end cap 50 to rotate about a pin 58, which is press fit into the end cap 50 on one side and seated within a cylindrical bearing surface in an end cylinder 60 forming part of the rotor 40. The rotor 40 may be rotated by any suitable rotary drive device or system, but in the illustrated embodiment, the end cylinder 60 includes or is partially formed of a magnetic material utilized in indirect driving of the rotor 40. The separation actuator 24 of the separation system includes a drive motor 62 exterior to the housing 38, which is coupled to turn an annular magnetic drive member 64 that includes a magnetic material that is attracted to the magnetic material of the end cylinder 60. As the annular drive member 64 is rotated, magnetic attraction between the end cylinder 60 and the annular drive member 64 effectively locks the rotor 40 to the exterior drive, causing the rotor 40 to rotate.

Rotation of the rotor 40 while fluid is present within the housing 38 causes Taylor vortices to arise in the gap 42. The Taylor vortices help to prevent cellular fluid components (e.g., red blood cells) from fouling or clogging the membrane 56, while encouraging smaller diameter fluid constituents (e.g., plasma) to pass through the pores of the membrane 56 to reach the central orifice or manifold 54. At the axial end of the rotor 40 opposite the end cap 50, the axial outlet port 44 communicates with the central orifice 54, such that the fluid constituents (e.g., plasma) passing through the membrane 56 and into the central orifice 54 may be transported to the axial outlet port 44. As for the fluid constituents that do not pass through the membrane 56, they travel along the length of the gap 42 from the inlet port 30 (positioned adjacent to one axial end of the rotor 40) to the tangential or red blood cell outlet port 46 (positioned adjacent to the other axial end of the rotor 40). Additional details concerning the design and functionality of a membrane separator that is suitable for the separation and collection of red blood cells may be found in PCT Patent Application Publication No. WO 2014/039086 A1.

The small-diameter fluid constituent (referred to herein as the "secondary fluid constituent," which may include plasma, but is not limited to plasma) separated by the membrane separator 12 flows from the axial outlet port 44, through a secondary fluid constituent flow path 66, and into a storage container 18, which may be of any suitable material compatible with storage of the secondary fluid constituent. Similarly, from the membrane separator 12, the concentrated red blood cells flow through the tangential outlet port 48 communicating with the gap 42 between the rotor 40 and the housing 38 and through a red blood cell flow path 48, which forms part of an outlet flow path 68. The separated red blood cells may be pumped through the outlet flow path 68 under action of a red blood cell or outlet pump 26b of the blood separation system. The outlet pump 26b may be configured and operate substantially the same as the inlet pump 26a or it may be differently configured (e.g., as a flexible diaphragm pump) without departing from the scope of the present disclosure. It will be seen that there is no pump associated with the secondary fluid constituent flow path 66, as the volumetric flow rate therethrough is instead equal to the difference between the volumetric flow rate of the inlet pump 26a and the volumetric flow rate of the outlet pump 26b.

If the red blood cell-containing fluid pumped into the membrane separator 12 is whole blood, then the membrane separator 12 will function to separate the blood into concentrated red blood cells and virtually cell free plasma. Packed red blood cells at approximately 80-85% hematocrit will be pumped out of the separator 12 through the red blood cell flow path 48. If the red blood cell-containing fluid is different from whole blood, then the nature of the separated red blood cells (e.g., their hematocrit) and the nature of the other fluid constituent from which the red blood cells are separated may vary.

Figure 3:
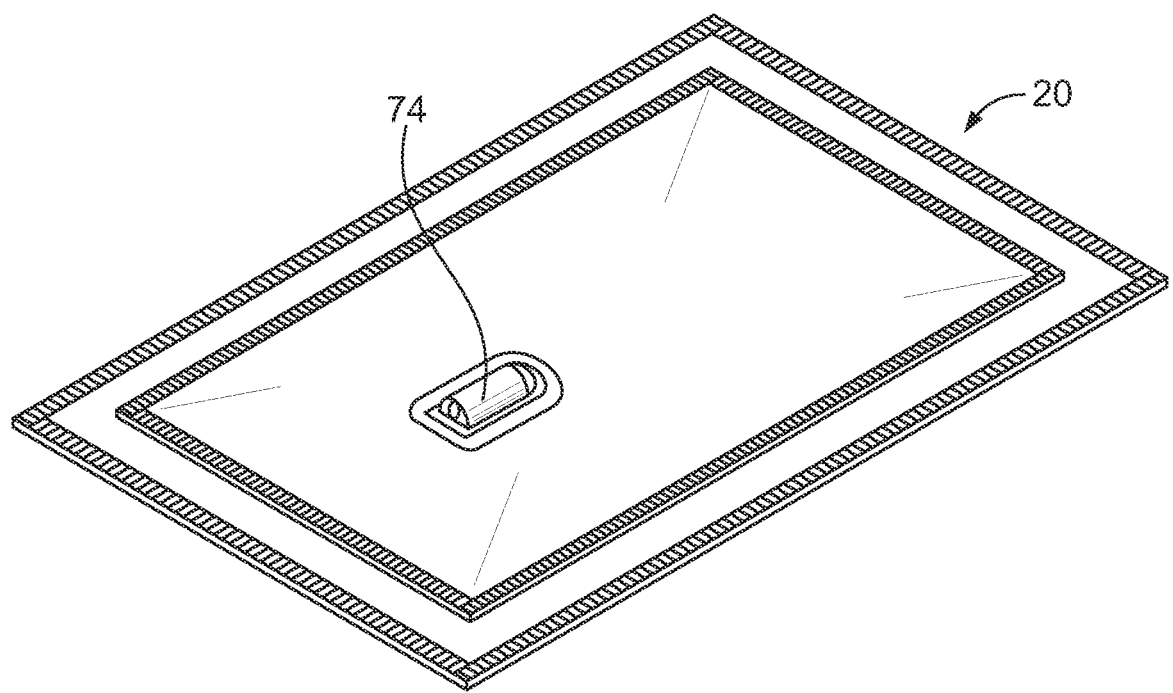
FIG. 3 is a front perspective view of a flexible luekoreduction filter of the fluid flow circuit of FIG. 1.
Figure 4:
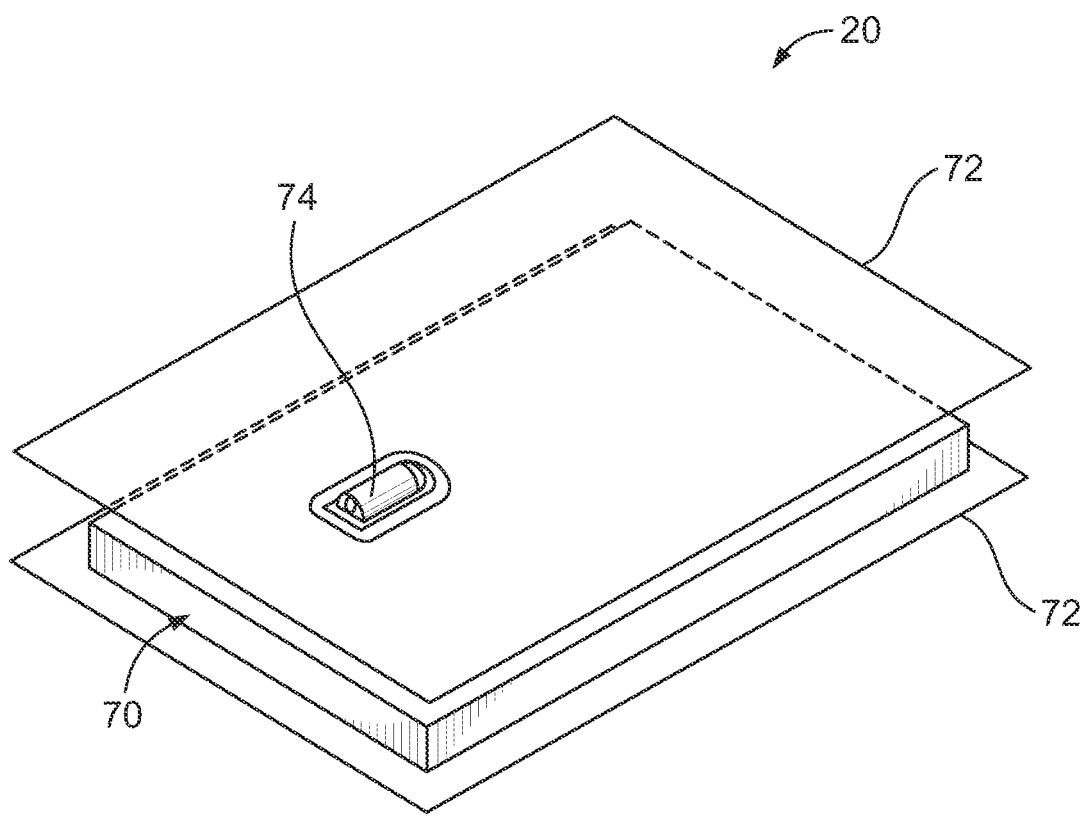
FIG. 4 is an exploded perspective view of the leukoreduction filter of FIG. 3.

For reducing the number of leukocytes that may be present in the separated red blood cells, the disposable fluid flow circuit 10 includes a leukocyte reduction filter or leukoreduction filter 20, which may be of any suitable well known construction for removing leukocytes from concentrated red blood cells without unduly causing hemolysis of red blood cells or reducing the number of red blood cells in the collected product. Examples of suitable leukocyte reduction filters may be found in U.S. patent application Ser. Nos. 14/222,961; 14/223,511; and Ser. No. 14/223,831, all of which are incorporated herein by reference. FIGS. 3 and 4 illustrate an exemplary leukoreduction filter 20, which includes a filter medium 70 positioned between two flexible walls 72 (FIG. 4), which are sealed together to prevent leakage of fluid passing through the filter 20. In the embodiment of FIG. 1, the filter 20 is associated with the outlet flow path 68, with the separated red blood cells flowing out of the membrane separator 12, through the red blood cell flow path 48 of the outlet flow path 68, and into the leukoreduction filter 20. The red blood cells pass from an inlet 74 of the leukoreduction filter 20 to an outlet (not illustrated), passing through the filter medium 70, which removes leukocytes from the red blood cells. After exiting the filter 20, the concentrated red blood cells flow through a continuation 76 of the outlet flow path 68 into a storage container 22, which may be of any suitable material compatible with red blood cell storage.

Figure 5:
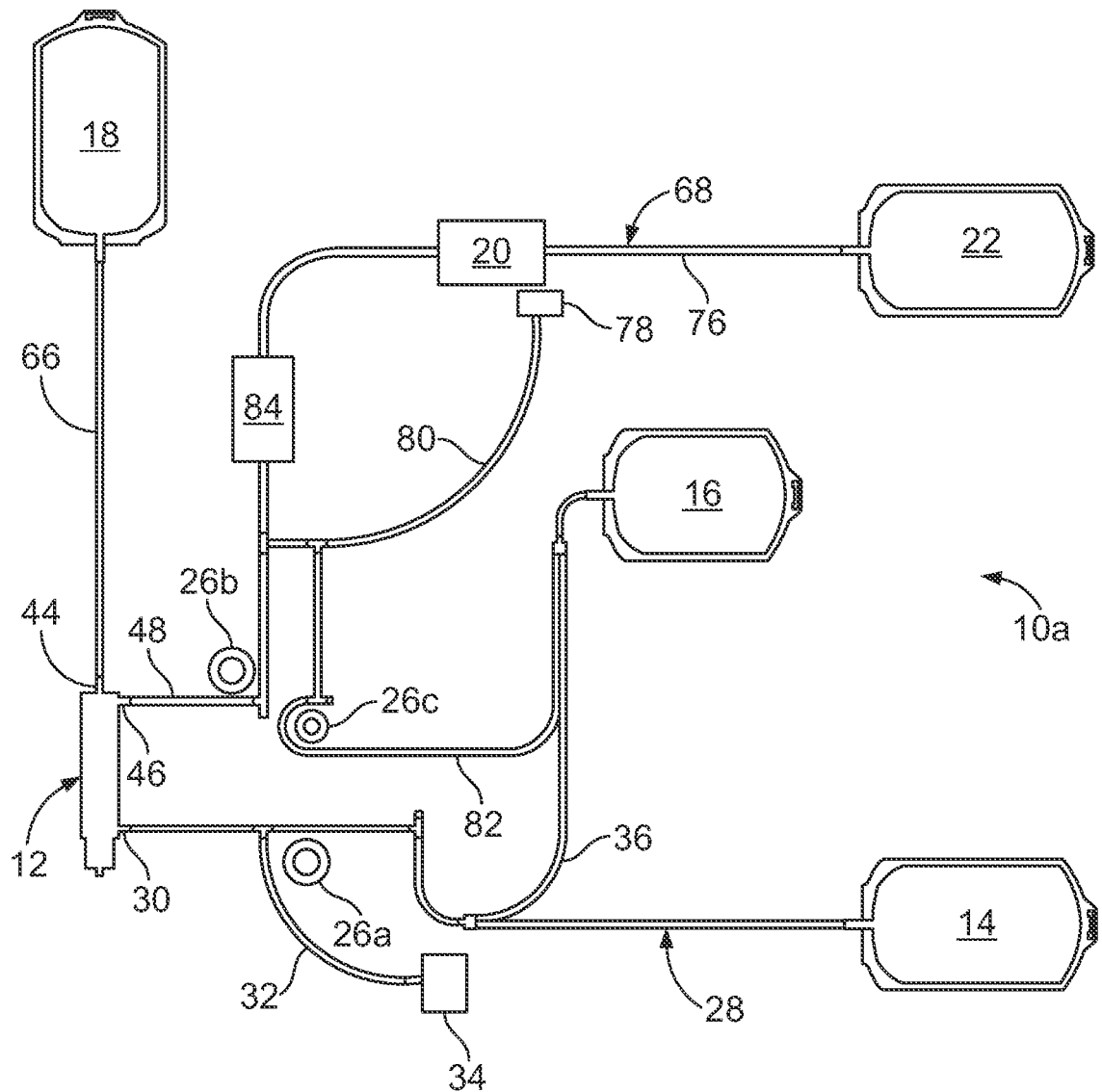
FIGS. 5-7 are front elevational views of other embodiments of an exemplary disposable fluid flow circuit according to an aspect of the present disclosure.

The force of the pump 26b pushing the concentrated red blood cells through the filter 20 helps to maintain and limit the processing time within a reasonable range, as compared, for example, to the time that would be required for gravity flow of concentrated red blood cells through a leukocyte reduction filter in a manual setting. While FIG. 5 shows the pump 26b positioned upstream of the leukoreduction filter 20, it should be understood that the pump 26b may also be positioned downstream of the leukoreduction filter 20 (i.e., between the leukoreduction filter 20 and the storage container 22). If the leukoreduction filter 20 is formed with flexible walls 72 (as illustrated in FIGS. 3 and 4), the outlet pump 26b may be controlled to operate to the point of causing the walls 72 to collapse, which better provides that all of the separated blood cells are flowed to the storage container 22 rather than being entrapped within the filter 20. If provided, a pressure sensor 78 associated with the outlet flow path 68 (e.g., associated via flow path branch 80) may wait for a particular pressure reading or condition (indicative of filter collapse) before ceasing operation of the outlet pump 26b.

The outlet flow path 68 may include additional components (e.g., valves or clamps) and junctions and branches, such as an additive junction and flow path branch 82, which leads to a red blood cell storage solution or additive container 16. The container 16 may include a storage solution or additive that may be pumped into the outlet flow path 68 by operation of an additive pump 26c of the separation system for addition to separated red blood cells in the storage container 22.

If provided, the pressure sensors 34 and 78 associated with the inlet flow path 28 and outlet flow path 68, respectively, may function to monitor the pressure within the associated flow path and send signals to a controller of the separation system that are indicative of the pressure within the flow path or paths being monitored. If the controller determines that an improper pressure is present within the fluid flow circuit 10 (e.g., a high pressure due to an occlusion of one of the flow paths), then the controller may instruct one or more of the pumps 26a-26c and/or one or more of the clamps or valves associated with the fluid flow circuit 10 to act so as to alleviate the improper pressure condition (e.g., by reversing the direction of operation of one of the pumps 26a-26c and/or opening or closing one of the clamps or valves). Additional or alternative pressure sensors may also be provided without departing from the scope of the present disclosure.

FIG. 5 illustrates a variation of the fluid flow circuit 10 of FIG. 1. The fluid flow circuit 10a of FIG. 5 differs principally from the fluid flow circuit 10 of FIG. 1 in that the outlet flow path 68 includes a microaggregate filter 84 positioned directly upstream of the leukoreduction filter 20 (i.e., between the red blood cell outlet port 46 of the membrane separator 12 and the inlet 74 of the leukoreduction filter 20). The configuration of the microaggregate filter 84 may vary without departing from the scope of the present disclosure (and will typically vary based on the nature and configuration of the leukoreduction filter 20 to better match the leukoreduction filter 20), but in one embodiment it may be provided as a filter sock having a length of approximately four inches and a pore size of approximately 80 microns. The configuration of the microaggregate filter 84 (e.g., the pore size) may also vary depending on the nature of the red blood cell-containing fluid, as microaggregates of differing diameters may be expected to arise from different fluids. By positioning the microaggregate filter 84 upstream of the leukoreduction filter 20, larger particles (e.g., microaggregates) are prevented from reaching and potentially clogging or impeding flow through the leukoreduction filter 20. Accordingly, the addition of a microaggregate filter 84 may have the effect of increasing the rate at which separated red blood cells pass through the leukoreduction filter 20, while also ensuring that a higher percentage of the red blood cells pass through the leukoreduction filter 20 without becoming entrapped therein.

Figure 6:
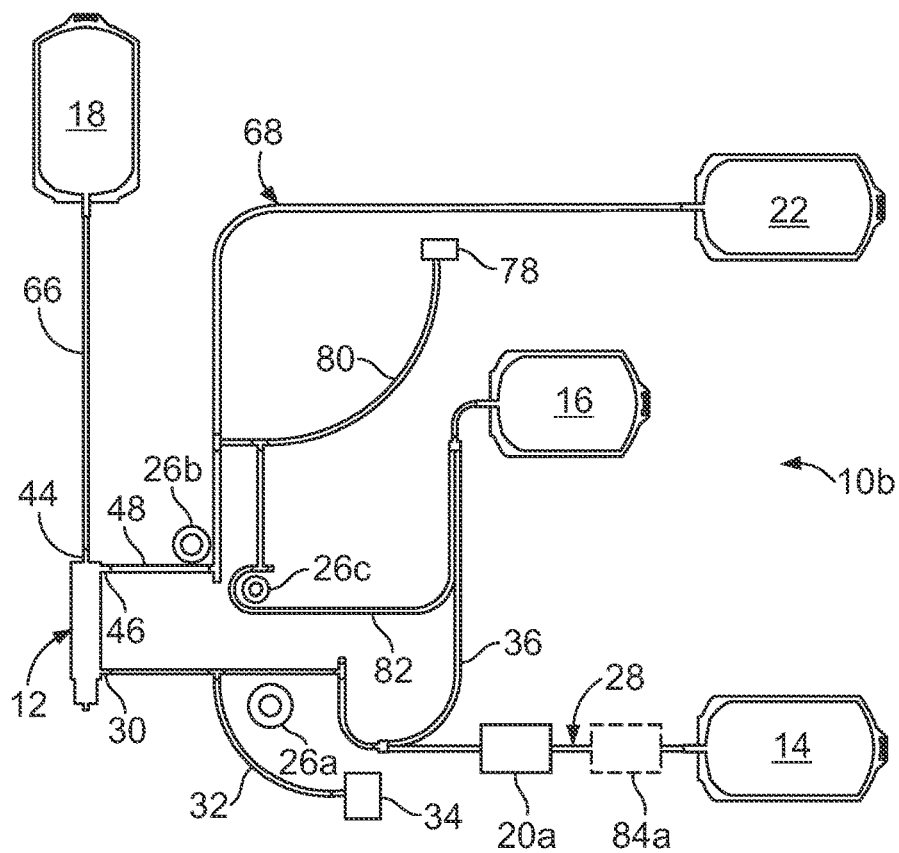

FIG. 6 illustrates another variation of the fluid flow circuit 10 of FIG. 1. The fluid flow circuit 10b of FIG. 6 differs principally from the fluid flow circuit 10 of FIG. 1 in that the leukoreduction filter 20 is absent from the outlet flow path 68, with a leukoreduction filter 20a instead being associated with the inlet flow path 28. As the nature of the fluid passing through the leukoreduction filter 20a (when positioned upstream of the membrane separator 12) is different from the nature of the fluid passing through the leukoreduction filter 20 (when positioned downstream of the membrane separator 12), the filter medium of the leukoreduction filter 20a may be configured to provide leukocyte reduction of anticoagulated red blood cell-containing fluid (e.g., anticoagulated whole blood), rather than separated red blood cells. Regardless of the nature of the red blood cell-containing fluid, its hematocrit and viscosity are typically less than the hematocrit and viscosity of the separated red blood cells passed through the leukoreduction filter 20 in the embodiment of FIGS. 1 and 5, meaning that decreased filtration time and incidence of clogging and/or fouling of the leukoreduction filter may be expected when positioning the leukoreduction filter 20a upstream of the membrane separator 12 instead of downstream. This may be especially advantageous when the anticoagulated red blood cell-containing fluid has been stored in the fluid source container 14 for an extended amount of time (e.g., up to three days or longer) prior to processing.

Figure 7:
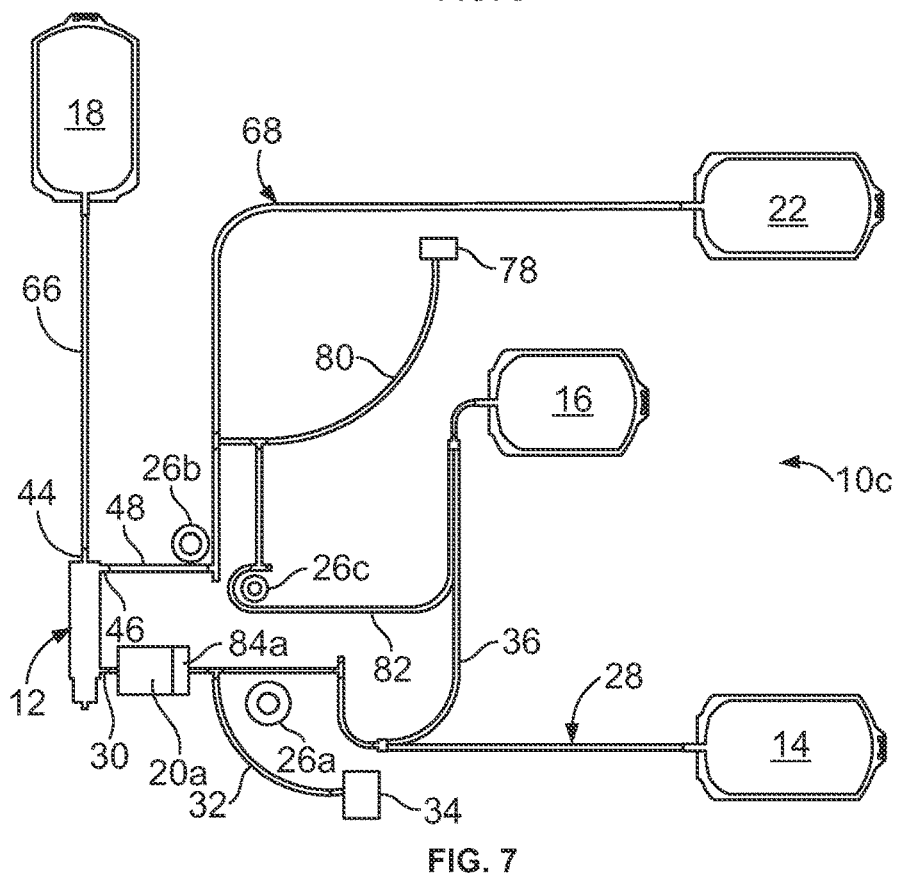

The leukoreduction filter 20a may be associated with the inlet flow path 28 in various locations without departing from the scope of the present disclosure. For example, FIG. 6 illustrates a leukoreduction filter 20a positioned upstream of the portion of the inlet flow path 28 configured to be acted upon by the inlet pump 26a of the separation system (i.e., between the inlet pump 26a and the fluid source container 14). In another embodiment of a fluid flow circuit 10c, which is shown in FIG. 7, a leukoreduction filter 20a is positioned downstream of the portion of the inlet flow path 28 configured to be acted upon by the inlet pump 26a of the separation system (i.e., between the inlet pump 26a and the membrane separator 12). One possible advantage of positioning the leukoreduction filter 20a upstream of the inlet pump 26a (as shown in FIG. 6) is to provide a clearer path between the inlet pump 26a and the membrane separator 12. In particular, optimized performance of the system may be controlled in part by monitoring pressure within the inlet flow path 28 (e.g., using a pressure sensor 34 associated with the inlet flow path 28 by branch 32). A leukoreduction filter 20a positioned upstream of the pump 26a avoids any pressure disruption between the pump 26a and the membrane separator 12, thereby possibly making it easier to precisely measure the pressure within the inlet flow path 28.

Regardless of the position of the leukoreduction filter 20a in the inlet flow path 28, the fluid flow circuit 10b, 10c may also include a microaggregate filter 84a positioned upstream of the leukoreduction filter 20a, as described above with respect to the embodiment of FIG. 5.

As described above with respect to a leukoreduction filter 20 associated with the outlet flow path 68, if the leukoreduction filter 20a associated with the inlet flow path 28 is formed with flexible walls, the inlet pump 26a may be controlled to operate to the point of causing the walls to collapse, which better ensures that all of the anticoagulated red blood cell-containing fluid is flowed to the membrane separator 12 rather than being entrapped within the filter 20a. If provided, a pressure sensor 34 associated with the inlet flow path 28 may wait for a particular pressure reading or condition (indicative of filter collapse) before signaling, via a controller (not shown), for cessation of operation of the inlet pump 26a. Similarly, if the fluid source container 14 has flexible walls, then the inlet pump 26a may be controlled to operate until the fluid source container 14 has been emptied of the red blood cell-containing fluid (which may be confirmed by a weigh scale associated with the fluid source container 14 or an optical monitor associated with the inlet flow path 28 or by any other suitable approach) and then operate for an additional amount of time after the fluid source container 14 has been emptied for improved filter volume recovery.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid flow circuit for separating an anticoagulated red blood cell-containing fluid into separated red blood cells and another fluid constituent, the fluid flow circuit comprising:
   a spinning membrane separator including an inlet port and a red blood cell outlet port and configured to separate an anticoagulated red blood cell-containing fluid into separated red blood cells and another fluid constituent;
   a fluid source container configured to contain an anticoagulated red blood cell-containing fluid;
   an inlet flow path in fluid communication with the inlet port and the fluid source container for flowing the anticoagulated red blood cell-containing fluid from the fluid source container to the inlet port; and
   a leukoreduction filter associated with the inlet flow path and positioned upstream of the spinning membrane separator.

2. The fluid flow circuit of claim 1, wherein the anticoagulated red blood cell-containing fluid is anticoagulated whole blood and the leukoreduction filter is configured to reduce the amount of leukocytes in the anticoagulated whole blood.

3. The fluid flow circuit of claim 1, further comprising a microaggregate filter positioned upstream of the leukoreduction filter.

4. The fluid flow circuit of claim 3, wherein the inlet flow path includes tubing connecting the leukoreduction filter to the microaggregate filter.

5. The fluid flow circuit of claim 3, wherein the microaggregate filter is incorporated into the leukoreduction filter.

6. The fluid flow circuit of claim 1, wherein
   a portion of the inlet flow path is configured to cooperate with an inlet pump, and
   the leukoreduction filter is positioned between said portion of the inlet flow path and the spinning membrane separator.

7. The fluid flow circuit of claim 1, wherein
   a portion of the inlet flow path is configured to cooperate with an inlet pump, and
   the leukoreduction filter is positioned between said portion of the inlet flow path and the fluid source container.

8. The fluid flow circuit of claim 1, wherein the leukoreduction filter includes flexible walls.

9. A method of separating an anticoagulated red blood cell-containing fluid into separated red blood cells and another fluid constituent comprising:
   providing an anticoagulated red blood cell-containing fluid in a fluid source container;
   flowing the anticoagulated red blood cell-containing fluid through an inlet flow path, through a leukoreduction filter associated with the inlet flow path and positioned upstream of a spinning membrane separator to leukoreduce the anticoagulated red blood cell-containing fluid, and into the spinning membrane separator;

separating the anticoagulated red blood cell-containing fluid into separated red blood cells and another fluid constituent; and flowing the separated red blood cells out of the spinning membrane separator via an outlet flow path.

10. The method of claim 9, wherein the anticoagulated red blood cell-containing fluid is anticoagulated whole blood.

11. The method of claim 9, further comprising flowing the anticoagulated red blood cell-containing fluid through a microaggregate filter prior to flowing the anticoagulated red blood cell-containing fluid through the leukoreduction filter.

12. The method of claim 11, wherein said flowing the anticoagulated red blood cell-containing fluid through a microaggregate filter prior to flowing the anticoagulated red blood cell-containing fluid through the leukoreduction filter includes flowing the anticoagulated red blood cell-containing fluid into, through, and out of the microaggregate filter, through a tubing, and into an inlet of the leukoreduction filter.

13. The method of claim 11, wherein the microaggregate filter is incorporated into the leukoreduction filter.

14. The method of claim 9, wherein said flowing the anticoagulated red blood cell-containing fluid through the inlet flow path and into the spinning membrane separator includes pumping the anticoagulated red blood cell-containing fluid through the inlet flow path and into the spinning membrane separator using an inlet pump positioned upstream of the leukoreduction filter.

15. The method of claim 14, wherein the fluid source container includes flexible walls, and said flowing the anticoagulated red blood cell-containing fluid through the inlet flow path and into the spinning membrane separator includes pumping the anticoagulated red blood cell-containing fluid into the inlet flow path from the fluid source container and continuing to operate the inlet pump after the fluid source container has been emptied of the anticoagulated red blood cell-containing fluid.

16. The method of claim 14, wherein said leukoreduction filter includes flexible walls, and said pumping the anticoagulated red blood cell-containing fluid through the inlet flow path and into the spinning membrane separator includes pumping the anticoagulated red blood cell-containing fluid through the inlet flow path until the leukoreduction filter collapses.

17. The method of claim 9, wherein said flowing the anticoagulated red blood cell-containing fluid through the inlet flow path and into the spinning membrane separator includes pumping the anticoagulated red blood cell-containing fluid through the inlet flow path and into the spinning membrane separator using an inlet pump positioned downstream of the leukoreduction filter.

18. The method of claim 9, further comprising storing the anticoagulated red blood cell-containing fluid in a fluid source container for up to three days prior to said flowing the anticoagulated red blood cell-containing fluid through the inlet flow path and into the spinning membrane separator.

* * * * *